(12) United States Patent
Neuss et al.

(10) Patent No.: US 10,905,573 B2
(45) Date of Patent: Feb. 2, 2021

(54) STENT

(71) Applicant: AndraTec GmbH, Munich (DE)

(72) Inventors: Malte Neuss, Bonn (DE); Gunter Kohl, Koblenz (DE); Jay Pillai, Johannesburg (ZA)

(73) Assignee: AndraTech GmbH, Munich (DE)

( * ) Notice: Subject to any disclaimer, the term of this patent is extended or adjusted under 35 U.S.C. 154(b) by 0 days.

(21) Appl. No.: 15/579,009

(22) PCT Filed: Jun. 3, 2016

(86) PCT No.: PCT/EP2016/062684
§ 371 (c)(1),
(2) Date: Dec. 1, 2017

(87) PCT Pub. No.: WO2016/193449
PCT Pub. Date: Dec. 8, 2016

(65) Prior Publication Data
US 2018/0140444 A1 May 24, 2018

(30) Foreign Application Priority Data
Jun. 3, 2015 (DE) .......................... 10 2015 108 835

(51) Int. Cl.
*A61F 2/915* (2013.01)
*A61F 2/24* (2006.01)
(Continued)

(52) U.S. Cl.
CPC ............ *A61F 2/915* (2013.01); *A61F 2/2418* (2013.01); *A61F 2002/061* (2013.01);
(Continued)

(58) Field of Classification Search
CPC .............................................. A61F 2250/0071
See application file for complete search history.

(56) References Cited

U.S. PATENT DOCUMENTS 9,192,492 B2 * 11/2015 Seguin .................... A61F 2/856
2001/0021872 A1 * 9/2001 Bailey ................... A61F 2/2418
623/1.24
(Continued)

FOREIGN PATENT DOCUMENTS

DE     202009012562 U1    12/2009
DE     102012001996 A1     8/2013

*Primary Examiner* — Megan Y Wolf
(74) *Attorney, Agent, or Firm* — Brooks Kushman P.C.

(57) ABSTRACT

The invention relates to a radially expandable stent (1) comprising a plurality of flexibly interconnected meandering ring elements (2, 3) defining a stent (1) having a proximal and a distal end and a longitudinal axis, wherein said ring elements (2, 3) being arranged side by side along the longitudinal axis of the stent and adjoining ring elements (2, 3) being attached to each other through connection elements (4), wherein connection elements (4) are arranged between at least two adjoining ring elements (2, 3), said connection elements each having at least one expandable expansion element with predetermined breaking point (10), wherein the expansion being possible in the longitudinal and/or transverse direction and the predetermined breaking points (10) only disrupting after the expansion element has been overstretched beyond its maximum expansion point.

12 Claims, 10 Drawing Sheets

(51) Int. Cl.
*A61F 2/07* (2013.01)
*A61F 2/06* (2013.01)

(52) U.S. Cl.
CPC ............... *A61F 2002/072* (2013.01); *A61F 2002/91541* (2013.01); *A61F 2002/91575* (2013.01); *A61F 2250/0071* (2013.01); *A61F 2250/0082* (2013.01); *A61F 2250/0096* (2013.01); *A61F 2250/0098* (2013.01)

(56) References Cited

U.S. PATENT DOCUMENTS

| | | | | |
|---|---|---|---|---|
| 2004/0127973 | A1* | 7/2004 | Mangiardi | A61F 2/91 623/1.15 |
| 2006/0276880 | A1* | 12/2006 | Neuss | A61F 2/91 623/1.15 |
| 2008/0269872 | A1* | 10/2008 | Lootz | A61F 2/915 623/1.15 |
| 2010/0280597 | A1* | 11/2010 | Hoerstrup | A61F 2/2418 623/1.26 |
| 2011/0224777 | A1* | 9/2011 | Von Oepen | A61F 2/91 623/1.16 |
| 2013/0238086 | A1* | 9/2013 | Ballard | D04H 1/42 623/1.46 |
| 2013/0317595 | A1* | 11/2013 | Obradovic | A61F 2/07 623/1.13 |

* cited by examiner

STENT

The invention relates to a radially expandable stent graft or vessel support which comprises a plurality of flexibly connected meandering ring elements defining a stent having a proximal and distal end and a longitudinal axis, the ring elements being arranged side by side along the longitudinal axis of the stent and adjoining ring elements being connected with each other by connection elements.

The stents or vessel supports proposed by the present invention are stents that can be radially widened along their entire length or in partial areas and are used for keeping open blood vessels or other organ pathways in human or animal bodies.

Stent grafts are generally implanted to permanently support the vascular wall in the region of stenoses, as a supporting structure of membranes to keep vessels open or of heart valves that can be implanted by minimally invasive methods. They are pressed onto a folded-up balloon and expanded within the vessel to a desired diameter by balloon dilatation.

However, since in children the maximum insertable diameter of a balloon catheter with a fitted stent is restricted by the limited diameter of the access vessel chamber of the femoral artery or femoral vein, a conventional stent can only be dilated to a maximum diameter of 6 to 8 mm. However, since the diameter of a pulmonary artery in adulthood can be as large as 30 mm, for example, conventional stents with a relatively small diameter would have to be removed by surgery on the heart-lung machine as the children grow older. This disadvantage is avoided by the stents which as proposed by the invention have predetermined breaking points, since they can be widened to any desired extent after disrupting the predetermined breaking points with another balloon. In this case, they have hardly any radial strength, but if necessary, the strength can be improved and achieved by implanting another stent having a larger diameter.

Other redilatable stent grafts have suture connections between zigzag wire framework, for example as described in DE 101 03 000, which dissolve after a certain time and thus allow further vascular growth. Disadvantageous in this case is a displacement of the segments sewn together when crimping onto a balloon and a low radial force.

According to U.S. Pat. No. 5,591,223 A, a re-expandable endoprothesis is formed from an initially rolled up, rigid tubular wire mesh being provided with a longitudinal slot. The longitudinal slot is also held together by resorbable connecting threads. By dissolving these connecting threads over time, this prosthesis can only be expanded in the area of this single slot. Due to its lack of flexibility, this endoprosthesis is not suitable for use in curvilinear vessel configurations such as in children and vessels situated close to the heart.

In publication WO 2011/032526 A1 a radially expandable vessel support with expansion elements is described, which allows a further expansion in a large diameter range while maintaining the radial force. The disadvantage here is that after circular dilatation and fracture of the expansion elements, these are capable of perforating the wall of the blood vessel like corkscrews.

Publication U.S. Pat. No. 5,591,223 A discloses a re-expandable vessel support which is provided with a ring segment having a growth joint. Said growth joint is bridged by connecting strips which may consist of absorbable wound suture and tear when a defined tensile force is exerted. The connecting strips are attached to the ring segment by welding, soldering or gluing.

It is thus the objective of the present invention to create a radially expandable stent graft which is not subject to any or only a slight shortening during its widening, which offers improved mobility in curved configurations and is less susceptible to buckling, has sufficient radial strength and at the same time can be dilated again by widening of at lease partial sections.

This objective is achieved by a radially expandable stent graft having the features specified in patent claim 1.

The inventive stent grafts consist of ring elements arranged next to each other, which have a meandering or zigzag shape, as well as connection elements that serve to attach the adjoining ring elements to each other. At least some of the connection elements are provided with predetermined breaking points, which in particular extend parallelly to the longitudinal axis of the stent, but can also be arranged transversely to it. A connection element can have predetermined breaking points both lengthwise and also crosswise. Inclined predetermined breaking points are also possible. In particular, however, longitudinally extending predetermined breaking points are considered recommendable that enable a partial or complete opening of the stent to take place during post-dilatation. For this purpose, the longitudinal predetermined breaking points also extend on and beyond the webs of the ring elements, which are attached to each other by means of the respective connection elements.

Overall, the inventive flexible, radial, re-expandable stent graft consists of a lattice-shaped stent framework with a meandering ring structure of small width provided with several predetermined breaking points arranged in the form of perforation lines or notches arranged in a circular, linear, transverse or spiral pattern. During fabrication and in the first implantation stage, these predetermined breaking points remain closed and firmly connected to each other, but can be broken up at a later stage by a further balloon dilatation in any desired way.

By breaking open the connection elements altogether or in individual partial sections of the stent at a later point in time, further growth of the vessel is made possible, if necessary also by further balloon dilatation or the implantation of an additional stent having a larger diameter in the areas of the existing stent.

As a result of breaking open the predetermined breaking points of a vessel support sideways, for example in the area of an especially marked zone with predetermined breaking points in the connecting elements, an improved side branch access can be created by local expansion in an advantageous way.

As proposed by the invention, the improved access to side branches can be achieved both by breaking open predetermined breaking points in partial sections of the stent as well as by arranging extended stent struts or by the omission of stent struts.

If the stent graft is additionally covered in whole or in partial sections with a biological or synthetic membrane, for example on the circumference, its attachment to the vessel support can be brought about by suturing, gluing, but also with special clamping and clip elements. These may also be conductively employed for the attachment of biological or synthetic tissue, membranes or foils and for laser-cut umbrella systems intended for the closure of heart wall defects. The same applies to implantable heart valves.

If the vessel support is covered with a membrane, it is of special advantage not to cover the two outer ring elements so that a membrane prolapse does not occur at the ends when expanding the stent.

The vessel supports proposed in accordance with the invention feature a plurality of connection elements with predetermined breaking function. These predetermined breaking functions can be limited, for example, to the connection elements of only two adjacent ring elements, for instance, in order to enable the stent to be opened up or folded open, but they may also be arranged between a plurality of ring elements, for example, in order to define a desired area and in this way enable fenestration operations to be performed. Another variant concerns the arrangement of predetermined breaking points over the length of the vessel support so that the stent can be opened up completely or partially. The predetermined breaking points can be arranged in parallel to the longitudinal axis of the stent, but may also follow a helix line that extends around the stent.

Of particular interest are predetermined breaking points, which are arranged on all the connection elements in a partial region of the stent and thus enable the opening of a window, for example in the region of branching-off blood vessels. In this case, it is advisable to arrange the predetermined breaking points both in the longitudinal direction of the extension of the vessel support and also transversely to it in order to be able to open a desired area.

Insofar as the inventive vessel supports are provided with a membrane that is sewn to the vessel support, relevant threads made of resorbable material or pure iron wire or tungsten wire can be used. The membrane itself can consist of a biological or synthetic material. The latter may have been applied by electrospinning.

In order to limit the length reduction during dilatation of the stents proposed according to the invention, a plurality of ring segments can be connected to adjacent ring elements by means of spiral, s-shaped or bow-shaped connection elements which elongate during dilatation. In particular, in the case of spiral, s-shaped or bow-shaped connection elements, there may be webs within the connection elements that are spaced at regular or other intervals in such a way that they allow a gradual or stepwise extension of the connection element. This is made possible, for example, by the fact that in the case of a spiral connection element, several webs are located at certain angular positions in the spiral, which, when overstretching takes place, successively break and, in this way, allow the connection element to be made longer in steps from a spiral to a more stretched state. The predetermined breaking point of the connector that ultimately allows a complete break-up of the connector, is then preferably located in the middle of the spiral, whereby other positions are also conceivable and possible. The same principle can also be applied to bent or convoluted connection elements. Another advantage of this embodiment is that the sometimes rather filigree structures of these convoluted connection elements are given additional stability through the connecting webs leading to a protection not only of these structures but also of the balloon when crimping the stent onto a balloon.

Preferred in this context are also bow-shaped connection elements arranged in pairs in opposite directions, which together with the adjacent struts of the ring elements form a star-shaped element. In spite of the multicellular structure's high flexibility, this results in high radial strength, which is even increased by a spiral or alternating arrangement of one or several star-shaped segments. The bending behavior of the stent or vascular support is also positively influenced by such elements.

The connection elements may also be designed in such a way that a lever arranged in the connection element causes the predetermined breaking points to be broken. The web in this case is attached to the connector for example in the form of a two-dimensional ball and socket joint, where both elements are connected by a connecting web—the predetermined breaking point—located between the two-dimensional joint ball and joint socket. This has the advantage that the design of the predetermined breaking point can be more stable because a leverage force acts on this point in the event of overexpansion. Correspondingly, this region has a higher strength in the not overstretched stent. An overstretching also leads to the disruption of the predetermined breaking point and, possibly, even more easily and in any case in a defined way. By selecting the lever, it is in fact possible within a given scope to specify the force required to break the predetermined breaking point. It is also beneficial that such a design of the predetermined breaking point via a lever permits a precise angular limitation of the maximum possible expansion of the stent without fracture in the corresponding connectors, which can additionally be defined by pre-defined latching points. The webs of the connection elements located between the individual ring elements preferably have a slightly smaller cross-section than the webs of the meandering or zigzag-shaped ring elements. The cross section of the connecting webs in this case amounts to about 60 to 80% of the cross section of the ring elements' webs. Conceivable and possible are optional combinations with the different shapes and designs of the webs of connection elements.

In the event that the predetermined breaking points consist of notches, said notches generally have a depth ranging between 30 and 50% of the web thickness of the connection elements on which they are arranged. Perforations, which as a rule are arranged linearly, have a diameter ranging approx. between 20 and 60% of the web width of the corresponding connection elements. The shape of the perforations can be round, triangular, rectangular or have a star pattern.

Customary materials can be used as material for the inventive stent or vessel support, in particular biocompatible metals such as iron, steel, tungsten, niobium, platinum, titanium, alloys of nickel and titanium as well as alloys containing at least one of these metals, such as platinum-iridium. In the event the vessel support itself is to be expandable, the use of a nickel-titanium alloy optimized for temperature by means of heat treatment is preferred.

In order to improve the ingrowth into the vessel wall, the stent/vascular support may be coated with a biocompatible material or with suitable medication to prevent hyperproliferation of the vascular wall or may release radiation as a result of exposure to irradiation or radioactive decay.

In addition, the stent or the covering may also consist of resorbable plastics, for example, of aliphatic polyesters such as polydioxanone.

The stents/vessel supports proposed by the invention are preferably formed from seamlessly drawn tubes in order to avoid tension and cracks, as is frequently encountered in the area of welding seams. The structures are preferably produced by laser or waterjet cutting, electrical discharge machining and electropolishing. In their original state after fabrication, the stents have a lattice-shaped structure that can be compressed by crimping onto a dilatation balloon and after implantation can be expanded by dilatation beyond the original state after fabrication. As a rule, the predetermined breaking points are only activated in the course of a post-dilatation or re-dilatation causing said points to be torn open. As required by the relevant application of the stent/vessel support proposed by the invention with its various embodiments, predetermined breaking points may also be dispensed with in special cases.

Insofar as the connection elements are designed to serve solely as clamping means for membranes, predetermined breaking points within the clamps can be dispensed with in these special cases.

Further characteristics and advantages of the invention can be seen from the following description of embodiment examples on the basis of the illustrations and figures showing essential inventive details as well as from the claims. The individual features can be realized here individually for themselves or to form several arbitrary combinations with variants of the invention. It goes without saying that illustrations and figures are only examples and that every special feature shown in an illustration belongs to the invention in any conceivable combination with features shown in other illustrations.

The following is shown in the figures, where.

Figure 1:
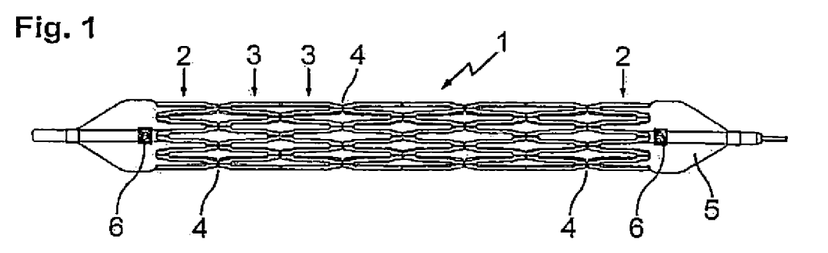
FIG. 1: is a side view of an embodiment of the invention crimped onto a dilatation balloon.

FIG. 1 shows a side view of an embodiment of the invention that has been crimped onto a dilatation balloon. The stent/vessel support 1 consists of a plurality of ring elements 2 and 3 which are connected to each other by connection elements 4. The ring elements 2 are arranged on the periphery, each having only one neighbor, while ring elements 3 have either a peripheral or an inner ring element to their neighbor. The connection elements 4 are connecting webs which start from the outer turning points of the ring elements and, in the case shown, extend to the outer turning points of the adjacent ring element 3.

The webs of connection elements 4 have perforations running in the direction of the longitudinal axis of the vessel support 1, which form a weakening zone resulting in a predetermined breaking point. The perforations continue through the adjacent parts of the webs of the ring segments 2, 3.

The stent 1 is attached to a commercially available balloon 5 which can be transported to the placement site by means of catheter and guidewire.

Figure 2:
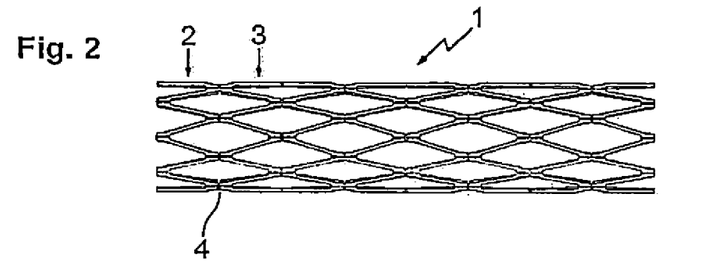
FIG. 2: illustrates a side view of the same embodiment as shown in FIG. 1 in a first expanded state, with the dilatation balloon being removed.

FIG. 2 shows the vessel support of FIG. 1 in a first implanted state with slightly expanded ring segments 2, 3 and intact connection elements 4. The dilatation balloon has been removed from vessel support 1.

Figure 3:
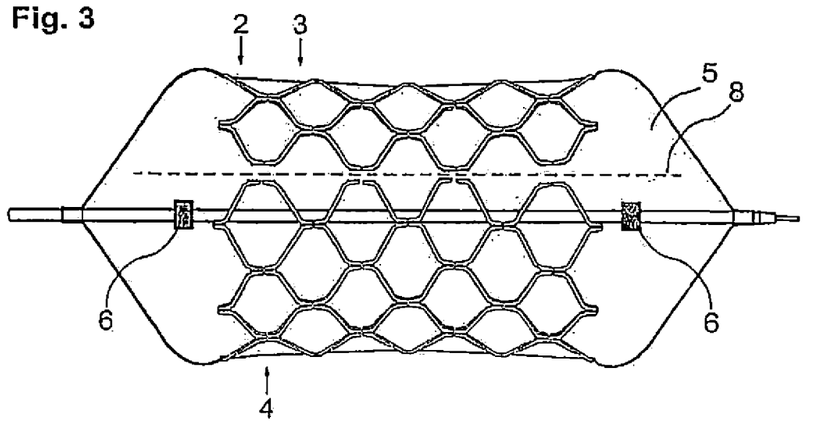
FIG. 3: in a further side view shows the embodiment illustrated in FIGS. 1 and 2 at maximum expansion with a pressure-resistant dilatation balloon of larger diameter and broken predetermined breaking points.

FIG. 3 finally shows the vessel support depicted in FIGS. 1 and 2 mounted on a dilatation balloon 5. In this figure, the dilatation balloon has a larger radius and in this way can further spread apart vessel support 1 until the perforation line 8, which runs parallelly to the longitudinal axis of vessel support 1, is torn or broken open.

For exact positioning of the implant or dilatation balloon, said balloon is equipped with markers 6 arranged proximally and distally to the vessel support 1.

Figure 6:
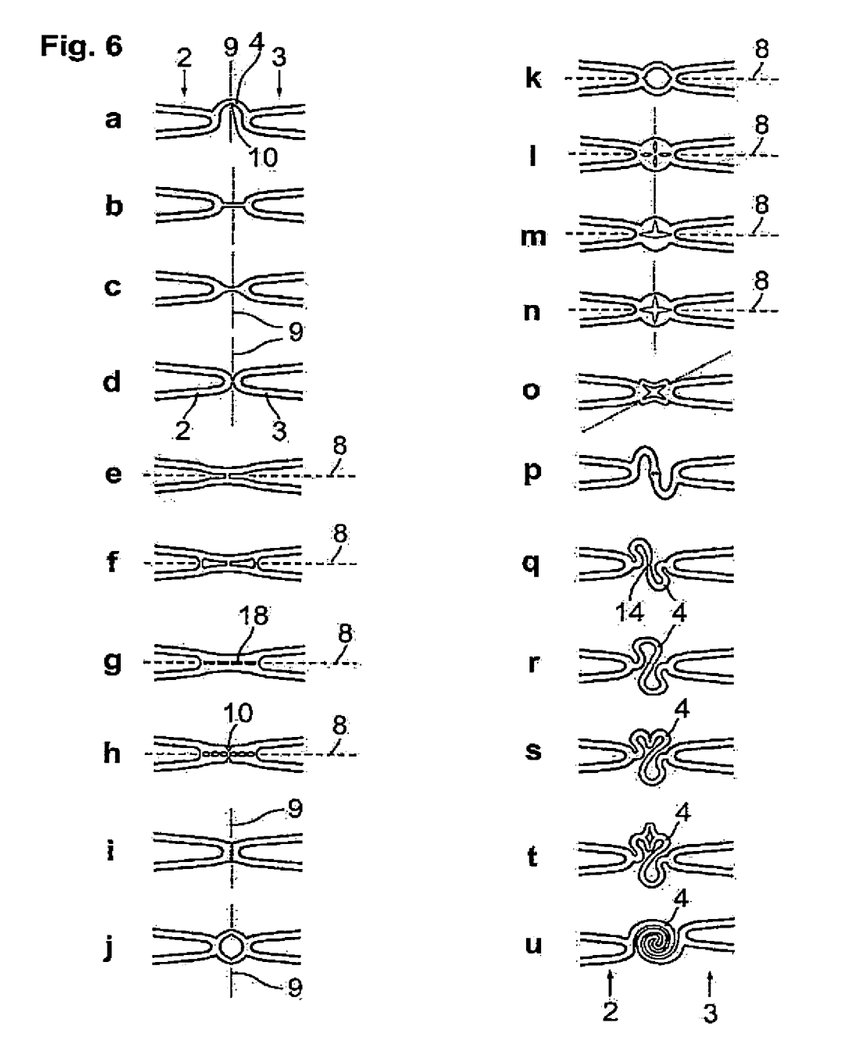
FIG. 6: illustrates different variants of connection elements, as they can be used according to the invention.

The connection elements 4 shown in FIGS. 1 to 3 correspond to the variant of the invention depicted in FIG. 6h.

The side view of the vessel support 1 illustrated in FIG. 3 with widening to a maximum diameter and broken connection elements 4 along the perforation line 8, which runs parallelly to the longitudinal axis of the vessel support 1, results in a vessel support 1 capable of only exerting reduced radial force but at the same time allowing further growth of the diameter of the respective vessel, such as the aorta or the pulmonary artery of a growing child. If necessary or thought expedient, an additional vessel support having a larger maximum final diameter may be implanted into the broken stent/vessel support 1.

Figure 4:
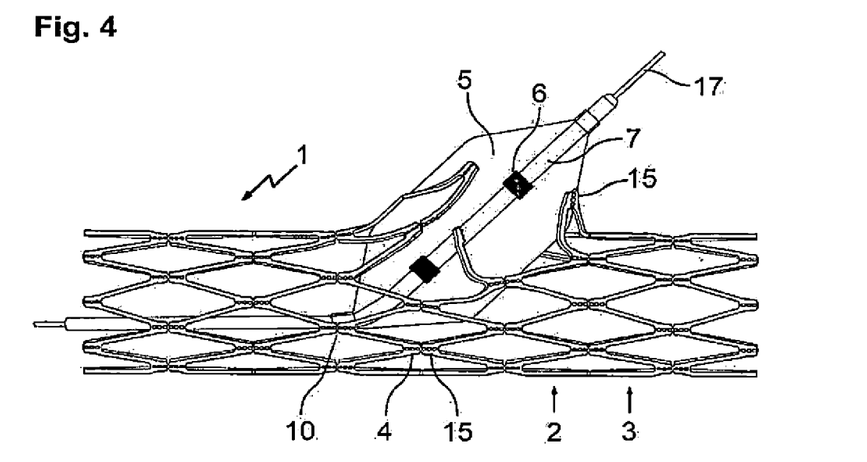
FIG. 4: as a side view depicts the embodiment of the invention according to FIG. 2, with a fenestration being implemented.

FIG. 4 shows the stent 1 of FIG. 2 and a dilatation balloon 5 introduced therein, which has been inserted through the side wall of vessel support 1 and dilated. As a result, the predetermined breaking points of the connecting webs of the relevant ring elements 2 and 3 have been broken open so that a window is created through which a blood supply can also be provided to a branching vessel.

Clearly shown are perforation lines 15 running in the longitudinal direction of the vessel support 1 and notches 10, which extend across the connecting webs 4 and enable the vessel support to be cut open transversely to the longitudinal direction.

The dilatation balloon 5 located at the tip of catheter 7 is advanced by means of a guidewire 17 and positioned in a well-aimed manner in the stent 1 that has already been implanted in the region of a vessel branch so that said stent 1 can be broken open in the region of the branch.

Figure 5:
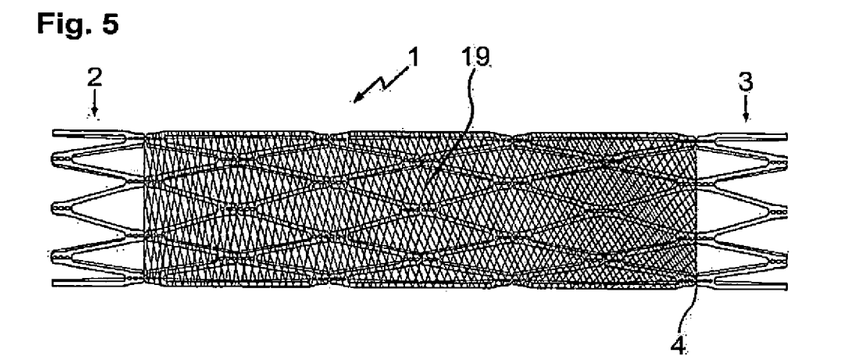
FIG. 5: shows the embodiment according to FIG. 2, covered with a membrane film.

FIG. 5 shows the stent represented in FIG. 2 with a tubular membrane 19 stretched over it, said membrane being used, for example, to shield a vascular anomaly, such as an aneurysm or perforation. For example, membrane 19 may be fabricated of Teflon or another material that is compatible with the body and may be fitted with a medication if considered expedient.

In FIG. 6 a plurality of variants of connection elements 4 are depicted that are provided with predetermined breaking points arranged between two ring elements 2, 3. Reference numerals 8 and 9 denote separation or perforation lines along which the respective connection element 4 is spread open. As is evident from the representations, connection elements 4 arranged between two ring elements 2, 3 can be designed almost arbitrarily and, for the generation of predetermined breaking points, are provided with notches 10, constrictions 14, perforations 18, and slot-shaped, circular, triangular, star-shaped or differently designed openings or weakening zones or, as shown in representations 6b, c and d, in another way, for example with webs that are strongly weakened in comparison to the webs of the ring elements 2, 3. In representations 6e to 6i the connection elements 4 are characterized by smooth transitions between two ring elements 2,3.

To compensate for the length reduction of the stent arising during dilatation, the connection elements 4 may be provided in the form of a curved arch (6a), S-shaped (6p, 6q), arbitrarily convoluted (6r to 6t) or spiral-shaped (6u). These curved connection elements 4 may additionally be designed so as to have predetermined breaking points in the form of notches or weakening zones.

Figure 7:
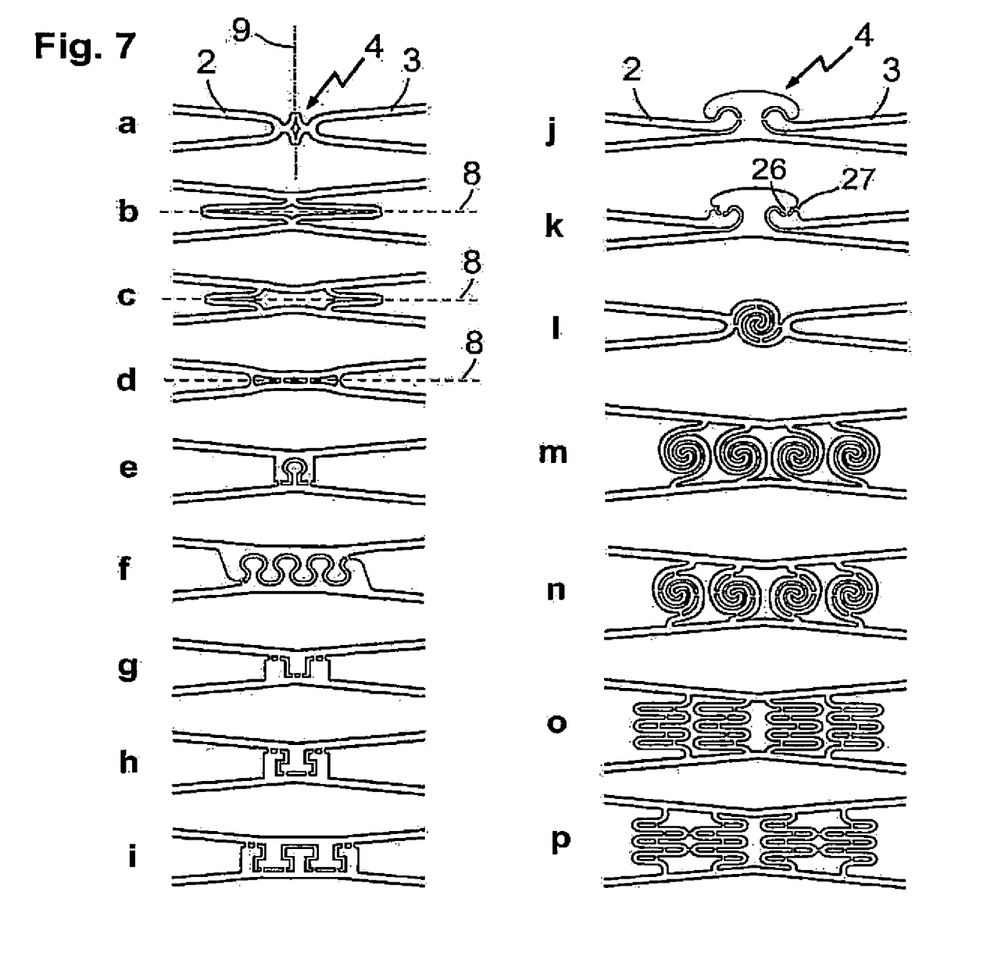
FIG. 7: illustrates further variants of connection elements, as they can be used according to the invention.

In FIG. 7 further variants of inventive connection elements 4 are shown that are arranged between ring elements 2, 3. The reference numerals coincide with those to indicated in FIG. 6. Representation a is another variant of a connection element 4 provided with a transversely arranged predetermined breaking point 9. Illustrations b to d show variants provided with longitudinal predetermined breaking point B. The variants e to i show several designs of the connection elements 4 that are also conceivable and in which the separation of the stent struts takes place gradually or stepwise by initially breaking the connecting webs within the connection element during overstretching, but a complete separation of the stent struts can only take place upon further expansion, as only this enables the spherical or T-shaped elements to exit their respective counterpart. The representations j and k show embodiments in which the stent webs in the connection element are arranged similarly to an articulated joint and connected via a connecting web. This arrangement allows the adjustment of defined leverage effects in the connection element when expanding the stent. Representation j shows a simple embodiment, in representation k the special arrangement provides for a buckling or break point 27 at the two-dimensional joint ball 26. The illustration l shows a variant of a connection element 4 that is of a spiral arrangement and can be stretched lengthwise. The spiral struts are connected to each other via connecting webs so that a gradual/stepwise extension of the connection element can be achieved when overstretching takes place. A further advantage of this embodiment is that the filigree spiral-shaped connector provides additional stability and thus protects this element against damage even during stent processing and, during crimping, also the balloon. The representations n to p show embodiments in which several of these elements, including the convoluted design form, are arranged next to each other and are also allowed to act in the longitudinal direction. Representation m shows a longitudinal arrangement of the spiral connectors without intermediate webs. A predetermined breaking point that causes a final separation of the longitudinal and/or transverse elements to take place is preferably located in the middle of the spiral or halfway along the convoluted connectors. However, any other meaningful position is also conceivable and possible.

Figure 8:
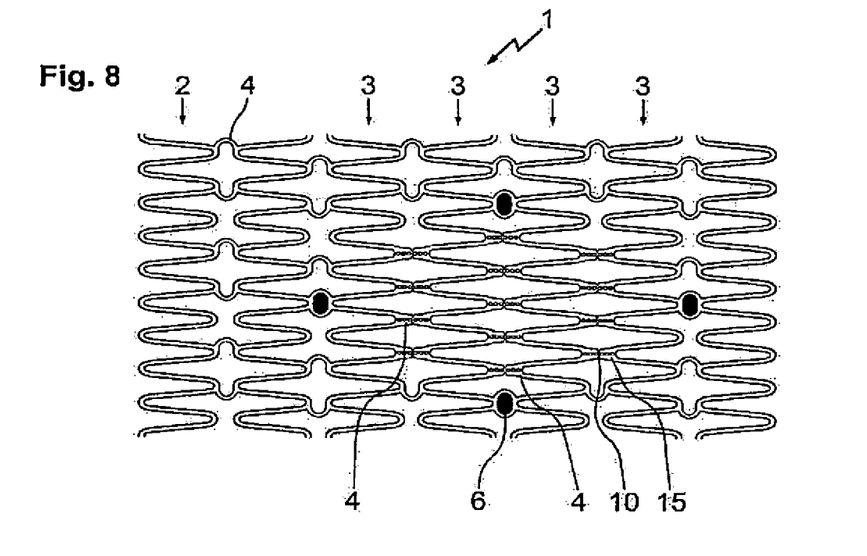
FIG. 8: shows a vessel support in spread out state with a region for fenestrations defined by connecting webs with predetermined breaking points.

FIG. 8 shows an embodiment of a stent/vessel support 1 in accordance with the invention, said stent being spread out and with a partial surface in which the connection elements 4 between ring elements 3 are provided with predetermined breaking points.

The zone designated for fenestration is delimited by four markers 6. Between these markers 6, all connection elements 4 are provided with a predetermined breaking point by means of perforation holes 15 arranged in longitudinal direction and with notches to generate a predetermined breaking point in circumferential direction. When a catheter balloon is expanded in the area of this fenestration zone, the connection elements 4 tear open along the predetermined breaking points and thus open the window, for example allowing access into a branching vessel.

In the areas in which no predetermined breaking points are provided in the connection elements 4, the stent as shown in FIG. 8 has curved connection elements 4, which with their open sides are facing each other in pairs and together with the adjacent loops of the ring elements 2, 3 form a star-shaped design that stands for good radial force.

Figure 9:
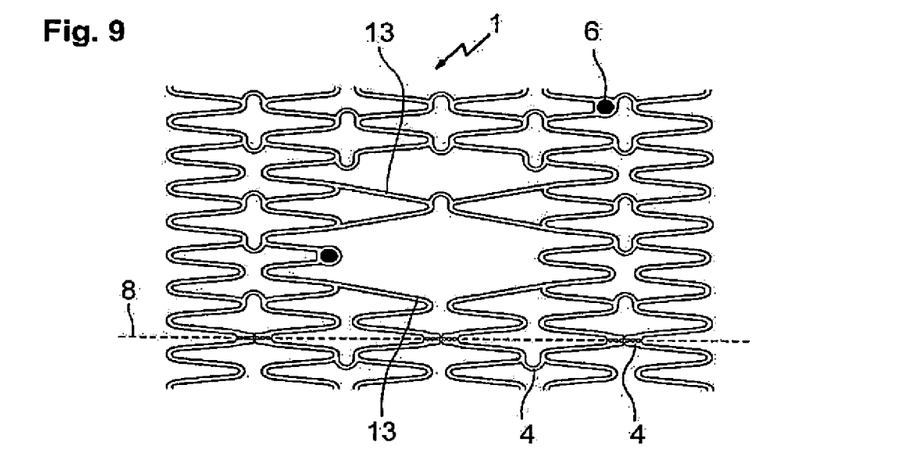
FIG. 9: illustrates a variant of a stent/vessel support according to invention with elongated webs in the central area.

FIG. 9 shows a stent 1 as proposed by the invention with webs 13, which are greatly extended in the central area in order to enable improved access to side branches in the dilated state. The stent 1 can be separated lengthwise along the dividing line 8, wherein the connection elements 4 along this dividing line are provided with two perforations which cause the weakening effect necessary for the separation.

FIG. 10a/b shows an inventive stent with a covering of 19 and predetermined breaking points in the connection elements 4, which run both lengthwise and transversely to it. For the fixation of the membrane 19, the stent 1 has a ring element 2', which is connected to the peripheral ring element 2 of the stent 1 via connecting webs 4', and can be folded back onto the membrane 19. Fixing pins 24 serve to secure the membrane 19.

FIG. 11a/b illustrates a variant of the embodiment depicted in FIG. 10a/b, in which end ring segment 2' is connected to the peripheral ring segments 2 by means of laterally offset connection elements 4'. The connection elements 4' extending diagonally sideways facilitate the folding of the ring element 2' onto the membrane 19.

Figure 10:
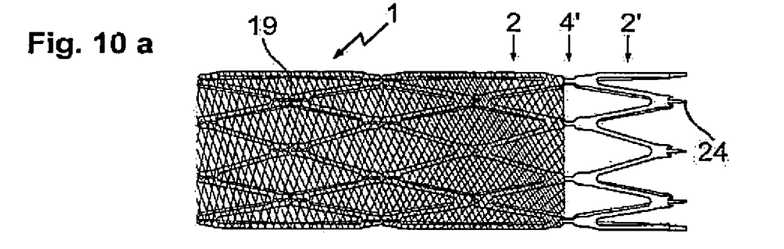
FIGS. 10a and 10b: show inventive stents, each with a membrane that can be fixed over the end segments.
Figure 11:
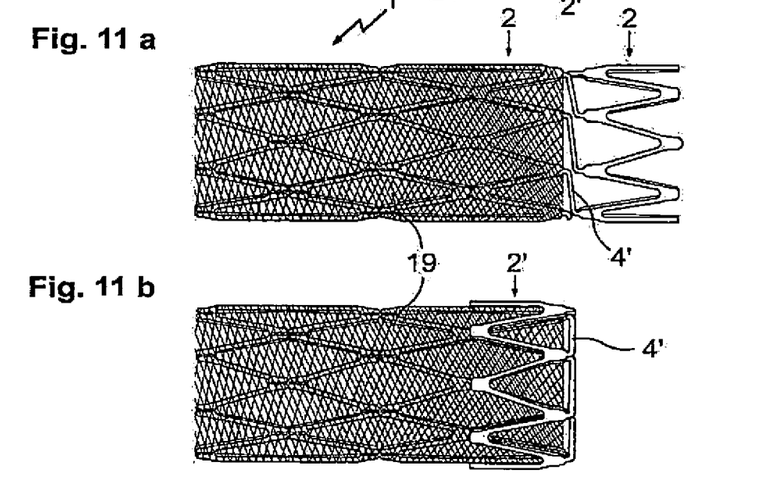
FIGS. 11a and 11b: are further variants of the embodiments shown in FIGS. 10a and 10b.

In the portion of the stent 1 located underneath the membrane 19, the embodiments according to FIG. 10 and FIG. 11 are provided with the inventive predetermined breaking points at the connection elements 4.

Figure 12:
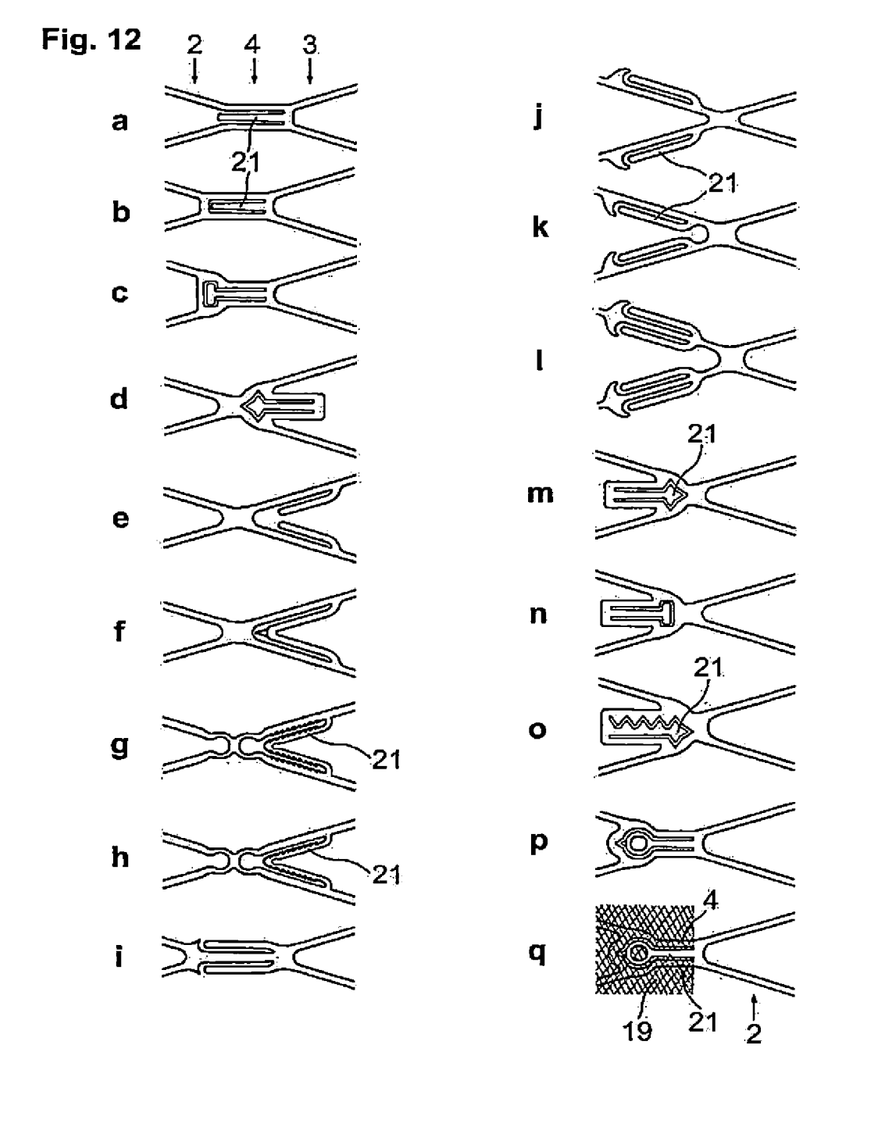
FIG. 12: shows variants of clamping elements by means of which a membrane can be fixed to the stent.

In FIG. 12 a plurality of clamping elements 21 are illustrated in the variants a to p, which serve to secure a membrane. The clamping elements 21 are webs notched out of a connection element 4 or a ring element 2, 3 and are flexibly movable against the connection element or ring element. This enables the membrane to be pushed under this springy clamping element 21 and thus held in place.

Advantageously, clamping elements 21 can be notched out both of connection element 4 as well as of a ring element 2 or 3. Said clamping elements are freely movable webs of almost any desired shape. An enlarged end in the form of a star, a hammerhead or a disc, with serrations or thorns may be provided and serves to improve the fixation of a membrane. Clamping elements 21 can be provided in pairs and run essentially in the longitudinal direction of the stent. In any case, a membrane is fixed by inserting it between the lattice structure of the stent and the freely movable webs of the clamping elements 21, see FIG. 12q.

Figure 13:
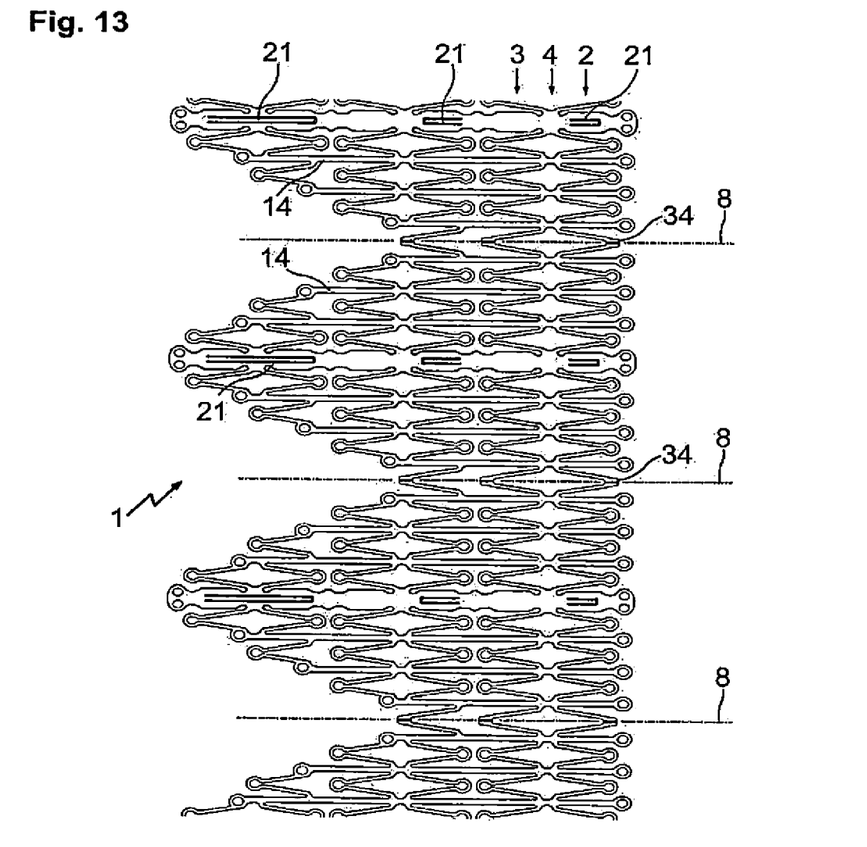
FIG. 13: shows an inventive stent that can be used, for example, for heart valve implants.

FIG. 13 depicts a vessel support 1 with a stent structure typically used for heart valves with peripheral ring segments 2, adjacent ring segments 3 and connecting webs 4. In this case, the connecting webs are often designed as straight webs that extend along the entire length of the stent 1 and thus define its length.

In the case shown here, connection elements 34 are arranged in the area of breaking lines 8 between webs of the ring elements 2 and 3. The predetermined breaking points are formed by perforation lines, which tear open during post-dilation and thus allow the valve to adapt to the vessel growth.

The stent 1 shown in FIG. 13 has springy webs 21 which are suitable for the fixation of stents supporting a heart valve in the surrounding vessel wall and thus prevent the stent from slipping or being displaced. Moreover, this stent may also be provided with other clamping elements as they are shown in FIGS. 12a to q, so that the material of the heart valve can be clamped in place. This eliminates the need for the otherwise conventionally applied bonding, wiring or sewing in of fixed or movable valve parts.

In order to reduce paravalvular leakage, it is also advantageous in this context to simply clamp in place a second cushion-like membrane by means of suitable clamping elements 21 inside and outside that exclusively serves sealing purposes at the lower margin of the stent 1.

Figure 14:
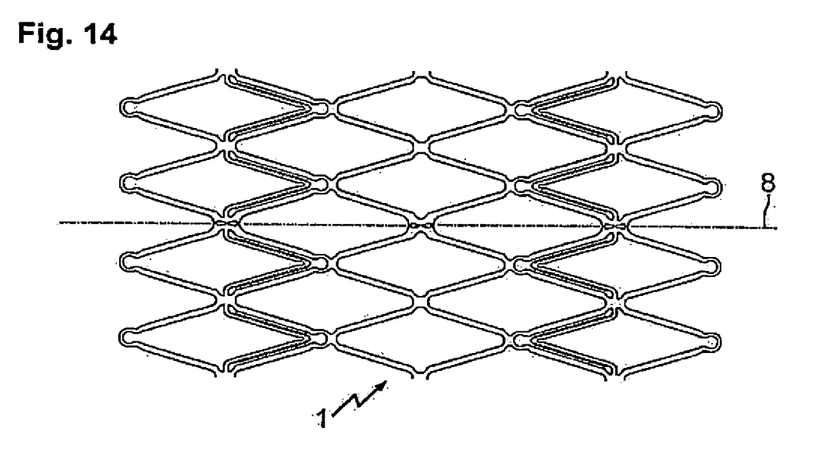
FIG. 14: shows an additional inventive stent that can be used, for example, for heart valve implants.

In FIG. 14 another embodiment of a vessel support is shown provided with clamping means intended for the fixation of a heart valve supporting membrane. The clamping means may correspond to one of the variants illustrated in FIG. 12 or also to a combination of these or other clamping means according to the invention.

Figure 15:
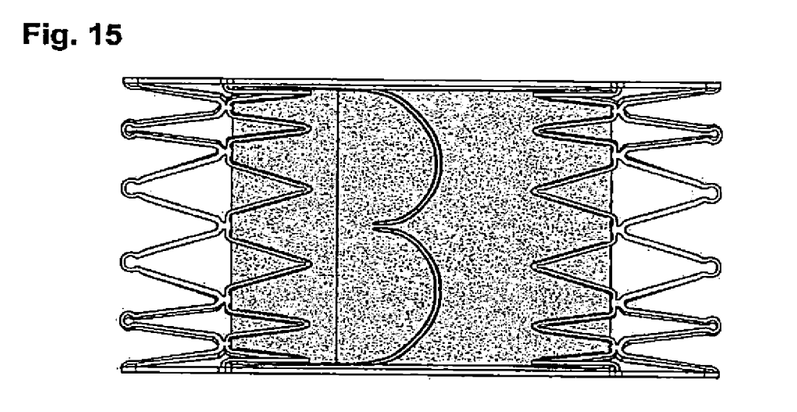
FIG. 15: illustrates the inventive stent according to FIG. 14 with a clamped membrane with heart valve.

FIG. 15 shows an example of how a cardiac valve-carrying membrane is clamped to a stent as shown in FIG. 14.

Figure 16:
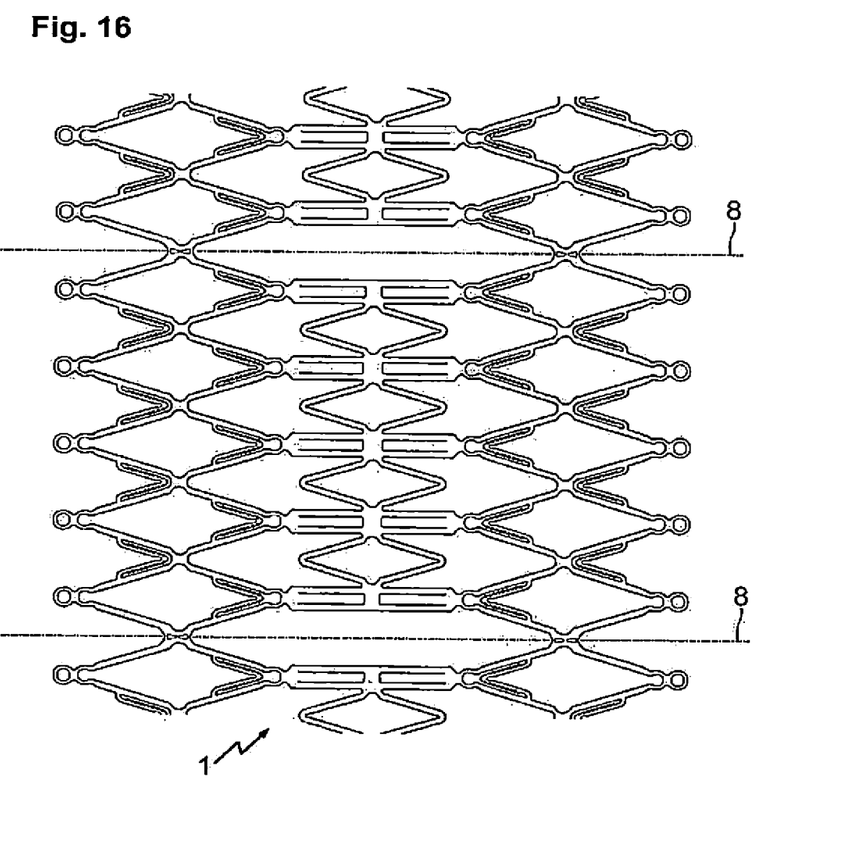
FIG. 16: shows another variant of a stent proposed by the invention that can be used, for example, for heart valve implants and has additional clamping elements for an additional membrane.

FIG. 16 shows another embodiment of a stent which, in addition to clamping means for the fixation of a cardiac valve-carrying membrane, has further clamping means for accommodating an additional membrane to be placed onto the outside of the stent. In addition, there are eyelets arranged on the outward-pointing arches of the peripheral ring elements through which one or more threads can be drawn, for example, in order to retract an already expanded vessel support into a catheter, for instance in the event an explanation or repositioning process is implemented.

The invention claimed is:

1. A radially expandable stent (1) comprising a plurality of flexibly interconnected meandering ring elements (2, 3) comprising struts defining the stent (1) wherein the stent comprises a proximal and a distal end and a longitudinal axis, wherein said ring elements (2, 3) are arranged side by side along the longitudinal axis of the stent and adjoining ring elements (2, 3) are attached to each other through connection elements (4), characterized in that connection elements (4) are arranged between at least two adjoining ring elements (2, 3), at least two of said connection elements (4) have an expandable expansion element with a predetermined breaking point (10), wherein expansion of the expandable expansion elements is possible in a longitudinal direction and the predetermined breaking points (10) of the expandable expansion elements only break after the expandable expansion element has been overstretched beyond a maximum expansion point, the at least two connection elements (4) are formed by two-dimensional ball and socket joints, wherein a ball and a socket are connected by a connecting web, the connecting web comprising the predetermined breaking point (10) of the expandable expansion element.

2. A stent according to claim 1, characterized in that the predetermined breaking points (10) on the at least two connection elements (4) extend in the direction of the longitudinal axis of the stent or in a helix-shaped way.

3. A stent according to claim 1, characterized in that the connecting webs extend transversely to the longitudinal direction in order to divide the stent in whole or in part.

4. A stent according to claim 1, characterized in that the predetermined breaking points (10) are arranged such that they enable a window to be broken open within the stent.

5. A stent according to claim 4, having connecting webs within said at least two connection elements (4) allowing for an area of possible fenestrations and having markers oppositely arranged in the area of possible fenestrations.

6. A stent according to claim 1 having outer ring elements (2) and ring elements (3) adjacent to the outer ring elements (2), the stent having a membrane attached thereupon, which leaves the outer ring elements (2) uncovered.

7. A stent according to claim 6, characterized in that the membrane can be fixed between an outer ring element (2) and a ring element (3) adjacent to the outer ring element by folding the outer ring element (2) down.

8. A stent according to claim 6, characterized in that the membrane is of tubular shape and is fixed with the aid of clamping elements to the ring elements (2, 3).

9. A stent according to claim 8, characterized in that the ring elements (2, 3) are provided with two inner rows and two outer rows of clamping elements, wherein a first membrane can be attached to the two inner rows of clamping elements inside of the stent (1) and a second membrane can be attached to the two outer rows of clamping elements outside of the stent (1).

10. A stent according to claim 6, characterized in that one or more membranes has 2 or 3 flap-like structures, at least one membrane of the one or more membranes being attached to the stent (1) by means of seams, gluing and/or clamping elements, the stent being capable of having a second cushion-shaped membrane arranged on the stent.

11. A stent according to claim 10, having peripheral ring elements and wherein the peripheral ring elements have outward facing arches, characterized in that eyelets are located on the outward facing arches of the peripheral ring elements to receive one or more threads in order to be able to retract an already expanded stent back into a catheter.

12. A stent according to claim 1, characterized in that said stent is provided at least in partial areas with an antiproliferative or anticoagulant coating.

\* \* \* \* \*